United States Patent [19]

Faasse, Jr.

[11] Patent Number: 4,744,355
[45] Date of Patent: May 17, 1988

[54] HINGED END WOUND DRESSING

[76] Inventor: Adrian L. Faasse, Jr., 10408 Braska Ave., Middleville, Mich. 49333

[21] Appl. No.: 866,269

[22] Filed: May 23, 1986

[51] Int. Cl.⁴ .............................................. A61L 15/00
[52] U.S. Cl. .............................................. 128/156
[58] Field of Search ................... 128/155, 156; 604/23

[56] References Cited

U.S. PATENT DOCUMENTS

| | | | |
|---|---|---|---|
| 2,292,995 | 8/1942 | Greenwoll | 128/156 |
| 2,629,378 | 1/1953 | Barton | 128/268 |
| 2,681,732 | 6/1954 | Brady | 206/56 |
| 3,038,597 | 6/1962 | Brady, Jr. | 206/56 |
| 3,143,208 | 8/1964 | Sizemore, Jr. | 206/56 |
| 3,260,261 | 12/1966 | Gallovich | 128/149 |
| 3,315,387 | 4/1967 | Heuser | 40/2 |
| 3,550,589 | 12/1970 | Wallerstein | 128/156 |
| 3,616,114 | 10/1971 | Hamaguchi | 161/39 |
| 3,645,835 | 2/1972 | Hodgson | 161/146 |
| 3,709,221 | 1/1973 | Reily | 128/156 |
| 3,885,560 | 5/1975 | Baldwin | 128/214 R |
| 4,094,316 | 6/1978 | Nathanson | 128/156 |
| 4,122,552 | 10/1978 | Tedford | 2/78 R |
| 4,176,664 | 12/1979 | Kalish | 128/156 |
| 4,192,299 | 3/1980 | Sabatano | 128/155 |
| 4,219,596 | 9/1980 | Takemoto et al. | 428/41 |
| 4,265,234 | 5/1981 | Schaar | 128/156 |
| 4,275,721 | 6/1981 | Olson | 128/133 |
| 4,281,650 | 8/1981 | Spiegelberg | 128/156 |
| 4,302,500 | 11/1981 | Flora | 428/284 |
| 4,341,208 | 7/1982 | Gordon | 128/156 |
| 4,367,252 | 1/1983 | Tordjman | 428/41 |
| 4,413,621 | 11/1983 | McCracken et al. | 206/441 |
| 4,418,822 | 12/1983 | Dotta | 206/441 |
| 4,420,519 | 12/1983 | Slemmons | 428/40 |
| 4,460,370 | 7/1984 | Allison et al. | 604/897 |
| 4,485,809 | 12/1984 | Dellas | 128/156 |
| 4,513,739 | 4/1985 | Johns | 128/156 |
| 4,545,371 | 10/1985 | Grossmann et al. | 128/132 D |
| 4,561,435 | 12/1985 | McKnight et al. | 128/156 |
| 4,598,004 | 7/1986 | Heinecke | 428/40 |

OTHER PUBLICATIONS

3M Package Publication.
Johnson & Johnson Products Inc., Package Publication.
Catalog Sheet Entitled "Wound Dressings by the Dozen".

*Primary Examiner*—Gregory E. McNeill
*Attorney, Agent, or Firm*—Price, Heneveld, Cooper, DeWitt & Litton

[57] ABSTRACT

The specification discloses a wound dressing in which the release liner halves are each divided into a release liner main body and a release liner edge strip. The release liner main body overlaps a portion of the edge strip and the two are hingedly secured together by a flexible hinge.

17 Claims, 2 Drawing Sheets

HINGED END WOUND DRESSING

BACKGROUND OF THE INVENTION

The present invention relates to wound dressings or like appliques. Wound dressings comprising adhesively coated, thin polymeric films have become popular because they allow the wound to breathe. However, because they are thin, they are difficult to apply to the wound without wrinkling or sticking on themselves.

In one type of wound dressing, the adhesively coated side of the polymeric film is covered by two pieces of release liner overlapping one another in a "plow fold" arrangement. One-half of the release liner is bent back on itself and the other half overlies the bent back portion. The user grasps the two halves of the release liner at the plow fold, grasping one-half between the thumb and first finger of each hand, and peels the release liner halves back. Before peeling the release liner completely free of the adhesive coated film, the user attempts to lay the film on the wound surface by manipulating the bandage via the release liner halves.

The problem with this type of bandage is that the release liners tend to peel away from the polymeric film before the film is in place on the wound. This, of course, leads to difficulties in applying the wound covering polymer film.

SUMMARY OF THE INVENTION

In the wound dressing or applique of the present invention, the problem of release liner prematurely peeling away from an adhesively coated covering layer is eliminated by providing a release liner having a main body and an edge strip hingedly joined by flexible hinge means. As one peels the main body of the release liner away from the covering layer, the main body folds back with respect to the edge strip at the hinge means, thereby minimizing the peeling forces exerted along the inside edge of the edge strip. This enables a user to control the covering layer by manipulating the main body of the release liner until the covering layer is applied to the desired surface. Then, force can be applied against the edge strip in the direction of the covering layer to fold the edge strip over and increase its tendency to peel away from the covering layer as a continuing force is applied to the main body of the release liner.

These and other objects, advantages and features of the present invention will be more fully understood and appreciated by reference to the written specification and appended drawings.

DESCRIPTION OF THE PREFERRED EMBODIMENT

Figure 1:
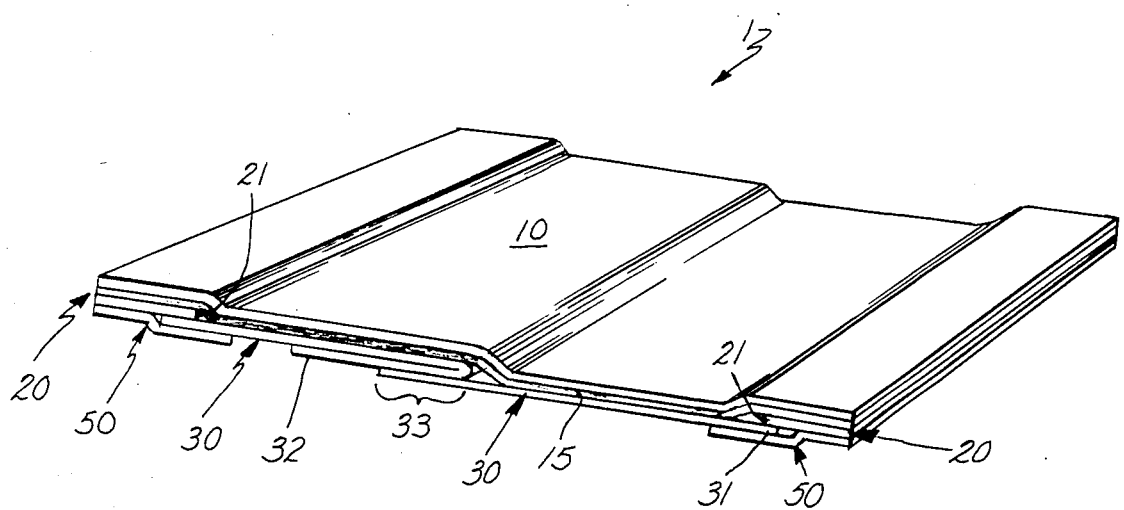
FIG. 1 is a perspective cross sectional view of the wound dressing or applique of the present invention, with the various layers substantially enlarged in thickness for illustrative purposes only.

In the preferred embodiment, wound dressing 1 of the present invention comprises a transparent polymeric covering layer 10 having an adhesive layer or surface 15 on one side thereof (FIG. 1). The adhesive surface is normally protected by a release liner, comprising a pair of release liner main bodies 30 each hingedly joined to a release liner edge strip 20 by means of a flexible hinge tape 50 (FIG. 1).

Polymeric film 10 can be any of the various polymeric films used in breathable wound coverings. Polyurethene film is one commonly used material. Copolyester film is used. Such films typically have thicknesses of from about 0.0005 inches to about 0.0015 inches for purposes of use in wound coverings.

The adhesive material 15 applied to polymeric film 10 is a conventional wound covering adhesive. Many different materials are available to those skilled in the art, most having proprietary formulas. Acrylic adhesives are operable. Such adhesives are usually applied to a thickness of from about 0.001 to about 0.0025 inches. It is desirable that adhesive layer 19 be sufficiently thin that the wound can breathe through the adhesive material and through polymeric film 10.

Release liner edge strip 20 and release liner main body 30 can be a conventional smooth surface paper material of the type typically used for release liners. Such liners typically comprise a heavyweight white paper coated on both sides with polyethylene for dimensional stability. One side of the liner is overcoated with a silicone release coating to permit ready separation of the adhesive coated film 10 from the liners 20, 30. Release liner 20, 30 is sufficiently thick to give some body to wound dressing 1 and make it easier to handle. Release liners typically have thickness of from about 0.004 to about 0.0075 inches.

Each release liner edge strip is located adjacent an edge of covering layer 10 and extends inwardly therefrom a short distance, as for example from about one-quarter to about three-quarters of an inch. One-half inch is probably applicable in dressings of most sizes. Release liner edge strips 20 are located opposite one another at opposite edges of covering layer 10.

Each release liner main body 30 overlaps its adjacent release liner edge strip 20 by a short distance at its outside end 31 (FIG. 1). The length of overlap is from about one-sixteenth to about one-eighth of an inch. This overlap insures that flexible hinge tape 50 will not directly engage release liner edge strip 20 at its inside edge 21. This in turn minimizes the chances that one will continue to peel release liner edge strips 20 back after main bodies 30 have been peeled back.

Release liner main bodies 30 overlap one another at the center of wound dressing 1 in a plow fold arrangement. One of the release liners 30 is folded back on itself to define a flap 32. A portion 33 of the other release liner half 30 then overlaps flap 32. This makes it easy for one to grasp the inside edges of release liner main bodies 30 to begin peeling them away from covering layer 10.

Figure 2:
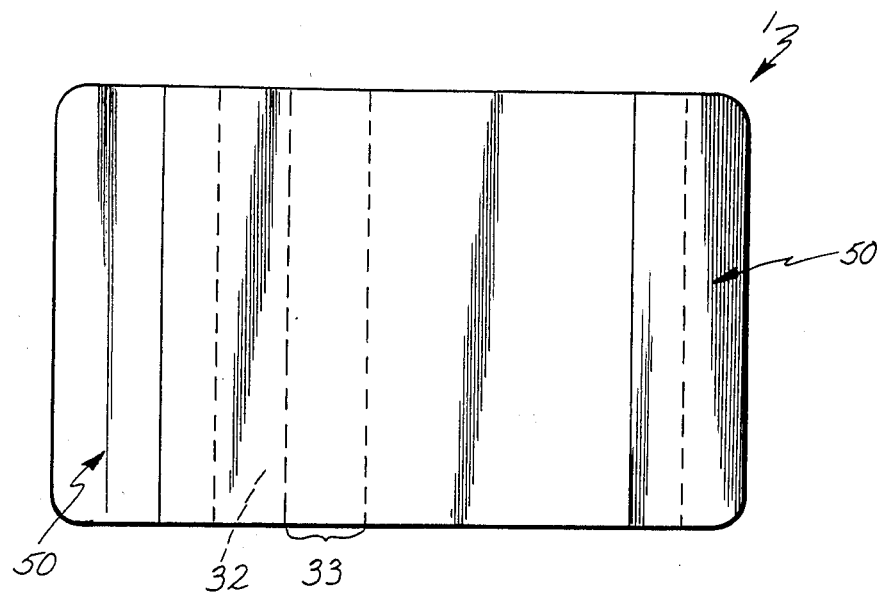
FIG. 2 is a bottom plan view of the wound dressing.

Hinge strips 50 are relatively narrow, i.e., from about three-eighths to five-eighths of an inch wide. Each is aligned so that it adheres both to a portion of release liner edge strip 20 and release liner main body 30 (FIGS. 1 and 2).

Hinge strips 50 are commercially available plastic film tapes commonly referred to as splicing tapes. It is presently preferred that the tapes be a 1 mil thickness polyester film with a silicone rubber adhesive applied to one side. The tape has a total thickness with adhesive of 2.5 mils, a tensile strength of 25 pounds per inch, an adhesion to steel of 35 ounces per inch and a tack level of 5.4. One such tape is available from The Kendall Company, Polyken Division, Boston, Mass., under the designation Plastic Film Tapes, Tape No. 781. Such splicing tapes are designed for splicing silicone coated materials and hence adhere readily to the nonsilicone coated sides of liners 20, 30.

Figure 3:
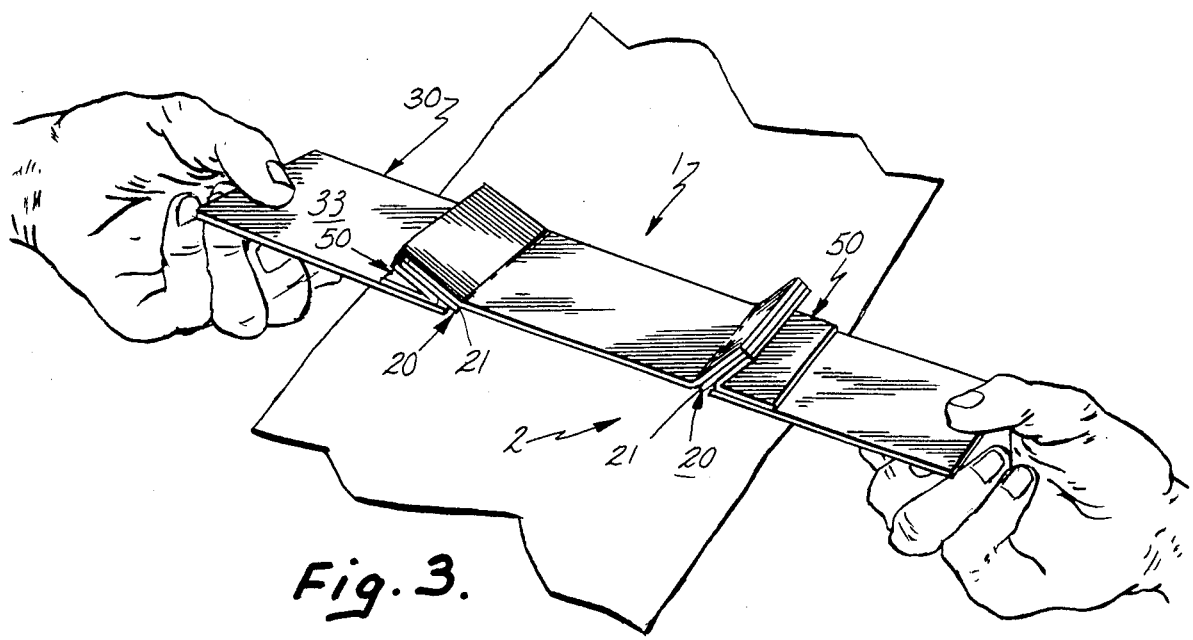
FIG. 3 is a perspective view showing the manner in which the wound dressing reacts when it is applied.

To use wound dressing 1, the user first grasps release liner main bodies 30 at their inside edge portions 32 and 33 respectively (FIG. 3). As the user peels back release liner main bodies 30, they are eventually peeled completely away from the adhesive surface 15 of wound covering layer 10. At this point, flexible hinges 50 simply fold back as illustrated in FIG. 3. As a result, no continuing peeling force is being applied to the inside edges 21 of release liner edge strips 20. There is thus much less tendency for release liner edge strips 20 to peel away from covering layer 10. This enables one to readily manipulate wound covering layer 10 by pulling slightly on release liner main body portions 30. The user does not need to worry about release liner edge strips peeling away from wound covering layer 10.

Figure 4:
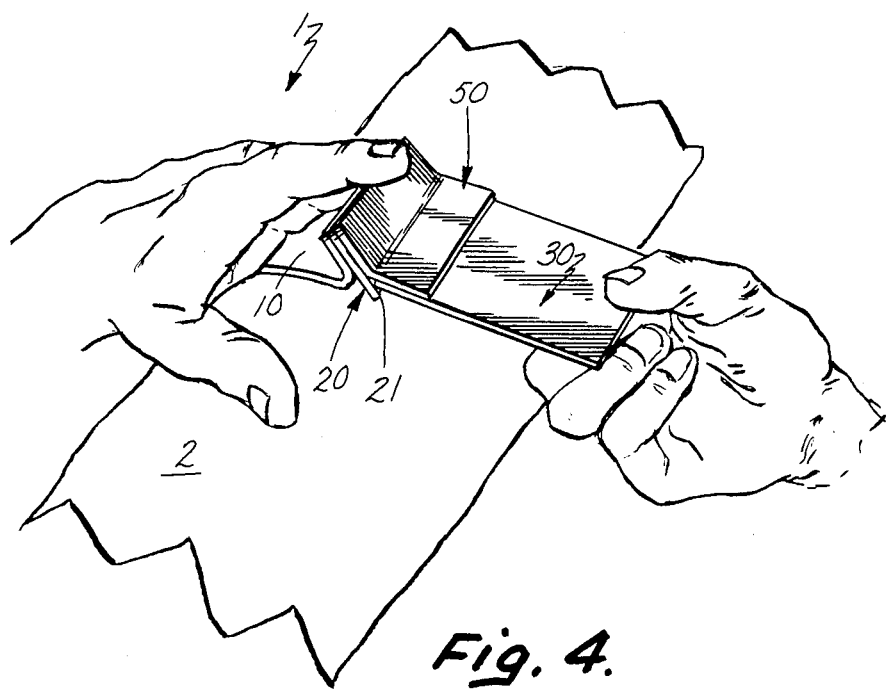
FIG. 4 is a perspective view illustrating the manner in which the release liner is ultimately separated from the wound covering layer of the bandage.

Wound covering layer 10 can be manipulated into position over the wound, as for example on an arm 2 as shown in FIGS. 3 and 4. Once wound covering layer 10 has been patted gently in place so it adheres to the substrate to which it is to be applied, one can effect separation of release liner edge strips 20 from wound covering layer 10 in the manner shown in FIG. 4. Basically, one folds release liner edge strip 20 over onto covering layer 10, while at the same time continuing to pull on release liner main body 30 (FIG. 4). As release liner edge strip 20 is forced over in the direction of wound covering layer 10, a peeling force is eventually applied along the inside edge 21 of edge strip 20 so that it is peeled away from covering layer 10.

Of course, it is understood that the foregoing is a preferred embodiment of the invention and that various changes and alterations can be made without departing from the spirit and broader aspects thereof as set forth in the appended claims.

The embodiments of the invention in which an exclusive property or privilege is claimed are defined as follows:

1. A wound dressing or like applique having a surface covering layer adhesively coated on one side, said adhesive coating being covered with a release liner, wherein the improvement comprises:

said release liner comprising a main body and an edge strip, said edge strip having an outside edge generally aligned with an edge of said covering layer and an inside edge spaced inwardly from said outside edge;

said main body and said edge strip being hingedly joined by flexible hinge means, said flexible hinge means overlying said main body and said edge strip whereby as one peels said main body of said release liner away from said covering layer, said main body folds back with respect to said edge strip at said hinge means, thereby minimizing the peeling force exerted along said inside edge of said edge strip and enabling a user to control said covering layer by manipulating said main body of said release liner until said covering layer is applied to the desired surface, at which time force can be applied against said edge strip in the direction of said covering layer to thereby fold said edge strip over and increase its tendency to peel away from said covering layer as a continuing pulling force is applied to said main body of said release liner.

2. The device of claim 1 in which said hinge means is secured to said edge strip along a line spaced outwardly from said inside edge of said edge strip whereby said hinge does not transmit force to said inside edge of said edge strip when one pulls on said main body of said release liner after it is peeled away from said covering layer.

3. The device of claim 2 wherein there are two of said edge strips, one located at each of two opposite edges of said main covering layer, and wherein said main body of said release liner is divided into two separate parts, one being hingedly joined to one of said edge strips and the other being hingedly joined to said opposite of said edge strips.

4. The device of claim 3 in which said halves of said main body release liner overlap one another in a plow fold arrangement.

5. The device of claim 4 in which said covering layer comprises a thin film of polymeric material.

6. The device of claim 2 in which said hinge means comprises a flexible adhesive tape, the adhesive bond between said tape and said release liner being substantially stronger than the adhesive bond between said covering layer and said release liner main body and edge strip.

7. The device of claim 1 in which said hinge means overlies and is secured to a portion of said main body and a portion of said edge strip at the juncture of said main body and said edge strip; said main body of said release liner overlapping at least a portion of said edge strip to cause said hinge means to be secured to said edge strip along a line spaced to the outside of said inside edge of said edge strip.

8. The device of claim 7 wherein there are two of said edge strips, one located at each of two opposite edges of said main covering layer, and wherein said main body of said release liner is divided into two separate parts, one being hingedly joined to one of said edge strips and the other being hingedly joined to said opposite of said edge strips.

9. The device of claim 8 in which said hinge means comprises a flexible adhesive tape, the adhesive bond between said tape and said release liner being substantially stronger than the adhesive bond between said covering layer and said release liner main body and edge strip.

10. The device of claim 7 in which said hinge means comprises a flexible adhesive tape, the adhesive bond between said tape and said release liner being substantially stronger than the adhesive bond between said covering layer and said release liner main body and edge strip.

11. The device of claim 1 wherein there are two of said edge strips, one located at each of two opposite edges of said main covering layer, and wherein said main body of said release liner is divided into two separate parts, one being hingedly joined to one of said edge strips and the other being hingedly joined to said opposite of said edge strips.

12. A wound dressing or like applique having a surface covering layer adhesively coated on one side, said adhesive coating being covered with a release liner, wherein the improvement comprises:

said release liner comprising a main body and an edge strip, said edge strip having an outside edge generally aligned with an edge of said covering layer and an inside edge spaced inwardly from said outside edge;

said main body and said edge strip being hingedly joined by flexible hinge means, said hinge means being secured to said edge strip along a line spaced outwardly from said inside edge of said edge strip whereby as one peels said main body of said release liner away from said covering layer, said main body folds back with respect to said edge strip at said hinge means, thereby minimizing the peeling force exerted along said inside edge of said edge strip and enabling a user to control said covering layer by manipulating said main body of said release liner until said covering layer is applied to the desired surface, at which time force can be applied against said edge strip in the direction of said covering layer to thereby fold said edge strip over and increase its tendency to peel away from said covering layer as a continuing pulling force is applied to said main body of said release liner, and said hinge does not transmit force to said inside edge of said edge strip when one pulls on said main body of said release liner after it is peeled away from said covering layer.

13. The device of claim 12 wherein there are two of said edge strips, one located at each of two opposite edges of said main covering layer, and wherein said main body of said release liner is divided into two separate parts, one being hingedly joined to one of said edge strips and the other being hingedly joined to said opposite of said edge strips.

14. The device of claim 12 in which said hinge means comprises a flexible adhesive tape, the adhesive bond between said tape and said release liner being substantially stronger than the adhesive bond between said covering layer and said release liner main body and edge strip.

15. The device of claim 12 in which said hinge means overlies and is secured to a portion of said main body and a portion of said edge strip at the juncture of said main body and said edge strip; said main body of said release liner overlapping at least a portion of said edge strip to cause said hinge means to be secured to said edge strip along a line spaced to the outside of said inside edge of said edge strip.

16. The device of claim 15 wherein there are two of said edge strips, one located at each of two opposite edges of said main covering layer, and wherein said main body of said release liner is divided into two separate parts, one being hingedly joined to one of said edge strips and the other being hingedly joined to said opposite of said edge strips.

17. The device of claim 15 in which said hinge means comprises a flexible adhesive tape, the adhesive bond between said tape and said release liner being substantially stronger than the adhesive bond between said covering layer and said release liner main body and edge strip.

* * * * *